United States Patent [19]

Kawai et al.

[11] Patent Number: 4,515,676
[45] Date of Patent: May 7, 1985

[54] CELL UNIT FOR OBSERVING ELECTROPHORESIS

[75] Inventors: Yoshio Kawai, Musashino; Kiyoshi Kitagawa, Komae, both of Japan

[73] Assignee: Kureha Kagaku Kogyo Kabushiki Kaisha, Tokyo, Japan

[21] Appl. No.: 556,322

[22] Filed: Nov. 30, 1983

[30] Foreign Application Priority Data

Dec. 10, 1982 [JP] Japan ................ 57-216540

[51] Int. Cl.³ .......................................... G01N 27/28
[52] U.S. Cl. ........................... 204/299 R; 204/180 R
[58] Field of Search ................. 204/180 R, 299 R

[56] References Cited

U.S. PATENT DOCUMENTS 3,948,753 4/1976 Arlinger ........................ 204/180 R
3,998,719 12/1976 Deml et al. .................... 204/180 R
4,046,667 9/1977 Goetz ............................. 204/180 R

FOREIGN PATENT DOCUMENTS 2808229 8/1979 Fed. Rep. of Germany ... 204/299 R

Primary Examiner—John F. Niebling
Assistant Examiner—B. J. Boggs, Jr.

Attorney, Agent, or Firm—Oblon, Fisher, Spivak, McClelland & Maier

[57] ABSTRACT

A cell unit for observing electrophoresis comprising a seal member in the form of an endless loop having penetrating holes passing therethrough between outside and inside of the loop at opposing positions of a circumferential wall thereof, a cell situated substantially in the inside of the loop, the cell defining therein a space for accommodating a liquid specimen, an electrophoretic property of which is to be observed, and including a pair of tubular end parts each having an opening communicated with the space and being fitted in a liquid-tight manner to the respective one of the penetrating holes in the seal members, and a pair of enclosing members, for defining, around the cell, a space for accommodating a liquid to control a temperature of the specimen in the cell, each enclosing member having an edge in the form the endless loop in close contact with a respective one end face, in the form of the loop, of the seal member ensures an easy mounting of the measurement cell at a desired position.

16 Claims, 5 Drawing Figures

CELL UNIT FOR OBSERVING ELECTROPHORESIS

This invention concerns a cell unit for observing electrophoresis and, more specifically, it relates to a cell unit of an apparatus for observing or measuring the electrophoretic behaviour or property of the cells based on microscopic observation.

In a known electrophoretic apparatus for the observation of the cell using the microscope, a liquid specimen including fine particles of body fluid components such a leukocyte and lymphocyte, or other particles found in a living body in a suspended condition in an appropiate electrolyte solution is filled within a measurement or observation cell and an electric field is applied to the liquid specimen for microscopically observing the velocities or the electrophoretic mobility of the particles. The cell unit for use in such electrophoretic apparatus comprises, in addition to the measurement cell, a conduit block having tubes for introducing the specimen into the measurement cell and a conduit block having tubes for discharging the specimen from the measurement cell, a thermostat bath as an enclosure means for defining, around the measurement cell, a space for accomodating a fluid to control the temperature of the liquid specimen in the measurement cell, and electrode chambers having a pair of electrodes for applying the electric field to the liquid specimen in the measurement cell.

An electrophoresis measurement cell unit of a type in which the measurement cell is made detachable to the conduit blocks is also known.

However, such a conventional measurement cell unit having the measurement cell detachable to the conduit blocks has a disadvantage on a point that it is difficult to exactly position the measurement cell and, accordingly, there is fear that the measurement cell may possibly be damaged when it is clamped upon assembling or mounting.

This invention has been made in view of the foregoings and the object thereof is to provide a cell unit for observing electrophoresis in which the measurement cell can be mounted easily at a desired position.

The above object of this invention can be attained by a cell unit for observing an electrophoresis comprising seal means in the form of an endless loop having penetrating holes passing therethrough between outside and inside of the loop at opposing positions of a circumferential wall thereof, a cell situated substantially in the inside of the loop, the cell defining therein a space for accomodating a liquid specimen, an electrophoretic property of which is to be observed, and including a pair of tubular end parts each having an opening communicated with the space and being fitted in a liquid-tight manner to the respective one of the penetrating holes in the seal means, and a pair of enclosing means for defining, around the cell, a space for accomodating a liquid to control a temperature of the specimen in the cell, each enclosing means having an edge in the form the endless loop in close contact with a respective one end face, in the form of the loop, of the seal means.

BRIEF DESCRIPTION OF THE ACCOMPANYING DRAWINGS

This invention is to be described in more details referring to the accompanying drawings, by which the foregoing and other objects, as well as the features of this invention will be made clearer in which.

DESCRIPTION OF THE PREFERRED EMBODIMENT

Figure 1:
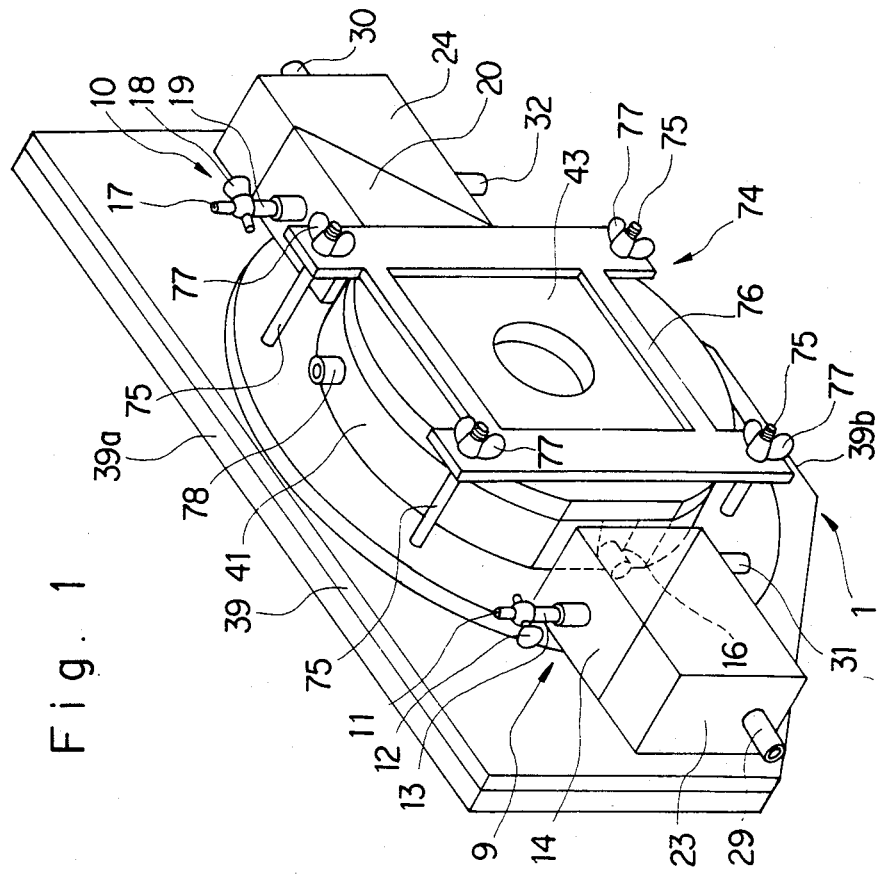
FIG. 1 is a perspective explanatory view of a cell unit as a preferred embodiment according to this invention.
Figure 2:
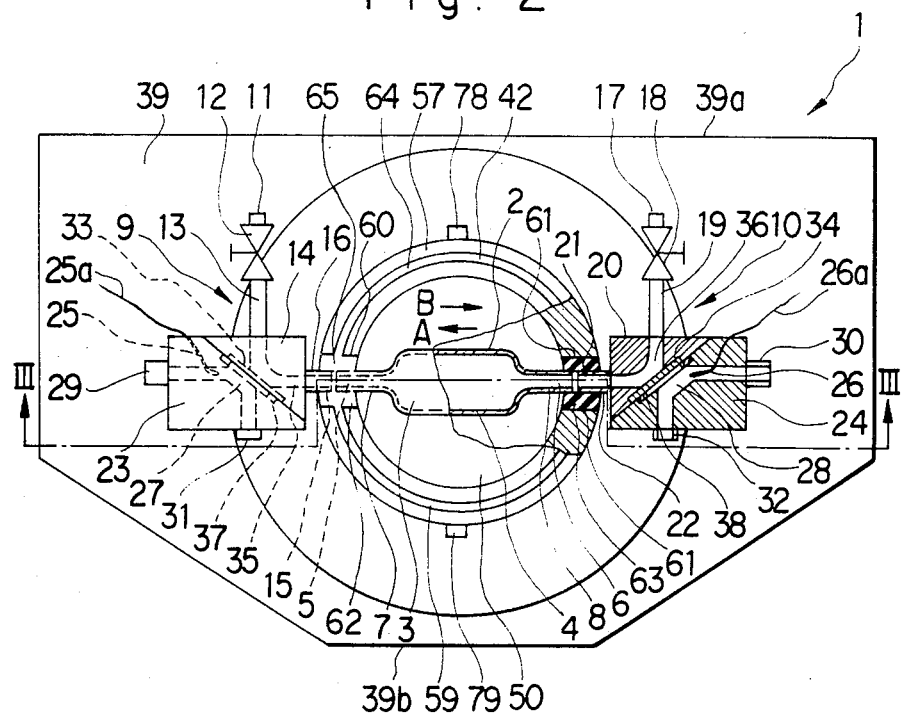
FIG. 2 is a partially broken front explanatory view of the cell unit shown in FIG. 1 with a front cover being removed.
Figure 3:
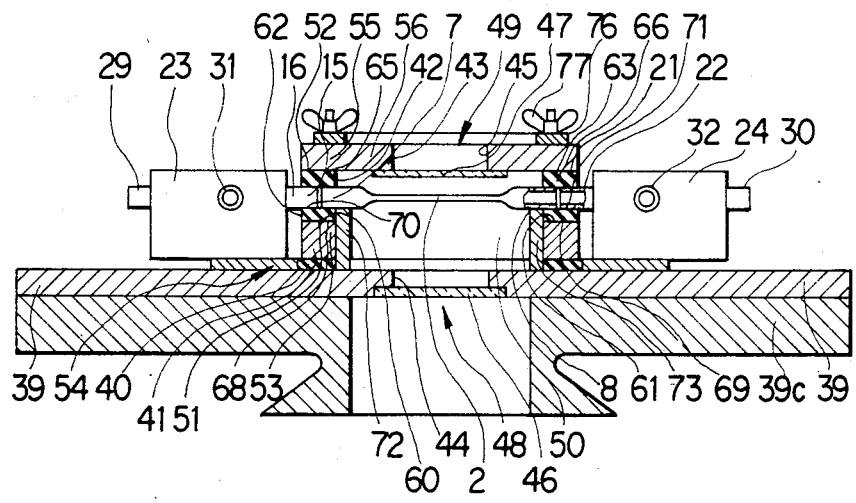
FIG. 3 is a cross sectional view taken along III—III in FIG. 2 for the illustration of the cell unit.

In a cell unit 1 for observing the electrophoresis of FIG. 1 through FIG. 3, a measurement cell is generally denoted by a reference numeral 2. The cell 2 comprises a cell main body 4 defining therein a wide and thin flat space or chamber 3 for accomodating a liquid specimen whose electrophoretic properties are to be observed or measured and tubular end parts 7, 8 respectively communicated at openings 5, 6 thereof with the space 3.

Conduit blocks 9, 10 are disposed on both lateral sides of the measuring cell 2 for introducing and discharging the liquid specimen into and out of the cell 2. The conduit block 9 comprises a tube 11 to be connected with a reservoir of the liquid specimen (not shown), a valve 12, a tube 13, a conduit body 14 connected with the tube 13 and the specimen inlet tube 16 connected at one end thereof to the conduit body 14 and at the other end 15 thereof to the tubular end part 7 of the cell 2. The conduit block 10 comprises a tube 17 to be connected with a reservoir of discharged liquid specimen (not shown), a valve 18, a tube 19, a conduit body 20 connected with the tube 19 and a specimen outlet tube 22 connected at one end thereof to the conduit body 20 and at the other end 21 thereof to the other tubular end part 8 of the cell 2.

The valve 12 is adapted to communicate and interrupt the passage in the tube 11 and the passage in the tube 13 and, while on the other hand, the valve 18 is adapted to communicate and interrupt the passage in the tube 17 and the passage in the tube 19.

Electrode housing 23, 24 respectively having electrode chambers 27, 28 where the electrodes 25, 26 are disposed respectively comprise tubes 29, 30 and tubes 31, 32 for passing the same electrolytic solution as the electrolytic solution of the liquid through the electrode chambers 27, 28. The electrode chambers 27, 28 in the electrode housing 23, 24 are separated from the passages 35, 36 in the conduit bodies 14, 20 by way of diaphragms or separation membranes 33, 34 allowing ions of the electrolytic solution to permeate therethrough. Numerals 37, 38 represent gaskets, and numerals 25a, 26a represent electrode leads.

The apparatus 1 includes a back plate or cover 39, an annular gasket 40, an annular frame member 41, an annular gasket or seal ring 42 as a seal means and a front cover 43.

At the central regions of the back cover 39 and the front cover 43, are formed windows 48, 49 having respectively apertures 44, 45 and transparent thin plates 46, 47 so that the motions or velocities of fine particles in the liquid specimen in the chamber 3 of the cell 2 can be observed by means of a microscope (not shown). The gasket 40 serves to provide a liquid-tight seal between the back plate 39 and the frame member 41, and the gasket 42 serves to provide a liquid-tight connection not only between the tube 16 and the cell 2 but also between the tube 22 and the cell 2, as well as to provide a liquid-tight seal between the front cover 43 and the frame member 41.

In the above-mentioned structure, a space or chamber 50, around the cell 2, for containing liquid to control the temperature of the specimen in the cell 2 is defined with the back cover 39, the gasket 40, the frame member 41, the gasket 42 and the front cover 43. A first enclosure means 54 comprises the back plate 39, the gasket 40 and the frame member 41, and is in close contact at an annular outer edge 53 with one of the opposing annular end faces 51, 52, that is, the annular end face 51 of the gasket 42 as the seal member. While on the other hand, a second enclosure means 56 comprises the front cover 43 which is in close contact at an annular outer edge 55 with the other annular end face 52 of the gasket 42 as the seal member. The enclosure means 54 comprising the back cover 39, the gasket 40 and the frame member 41 in the illustrated embodiment may alternatively be made of a one integral member, or the other enclosure means 56 may be formed by assembling a plurality of separate members. Furthermore, an annular recess for receiving the annular gasket 42 may be formed on the surface of the front cover 43 at the side facing to the chamber 50.

Figure 4:
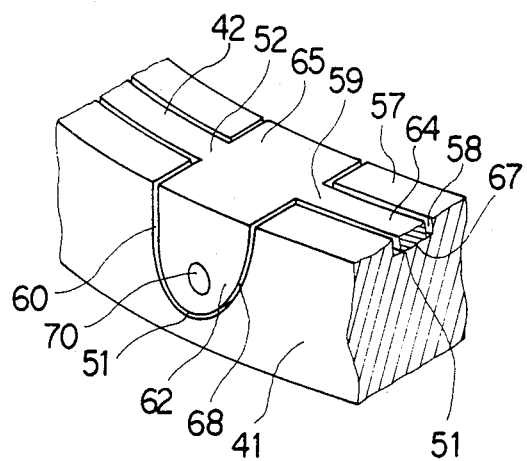
FIG. 4 is a perspective explanatory view showing a part of a gasket used in the coil unit shown in FIGS. 1 to 3.

Referring to the gasket 42 more specifically, the gasket 42 comprises, as shown in FIGS. 2 to 4, an annular gasket part 59 just fitted into a relatively wide and shallow annular groove 58 formed at the central part of an annular end face 57 of the frame member 41 and semi-cylindrical or U-shaped profile of thick gasket parts 62, 63 just fitted into U-shaped recesses or concaves 60, 61 formed at the opposing side walls of the frame member 41 while extended from the inner to the outer circumferential surfaces of the frame member 41. The gasket 42 is made, for example, of plastics, natural or synthetic rubbers.

The annular end face 52 of the gasket 42 in close contact with the front cover 43 as the enclosure means 56 comprises the annular end face 64 of the gasket part 59 and flat surfaces 65, 66 of the gasket parts 62, 63. While on the other hand, the annular end face 51 of the gasket 42 in close contact with the enclosure means 54 comprises the annular end face 67 of the gasket part 59 and U-shaped surfaces 68, 69 of the gasket parts 62, 63 respectively in close contact with the circumferential walls of the groove 58 and the grooves 60, 61 of the frame member 41. The surfaces 68, 69, preferably, have a generally arcuate configuration but they may be in the form of a square, U-shaped or like other configuration.

The gasket parts 62, 63 integral with the gasket part 59 have radial penetrating holes 70, 71 respectively at opposing positions of the circumferential wall of the gasket 42. The radial hole 70 has the end 15 of the tube 16 and the tubular end part 7 of the measuring cell 2 fitted thereto respectively in a liquid-tight manner from the radially outer and inner sides with respect to the annular gasket part 59. The radial hole 71 has the end 21 of the tube 22 and the end 8 of the measuring cell 2 fitted thereto respectively in a liquid-tight manner from the radially outer and the inner sides with respect to the annular gasket part 59.

The gasket 42 situated as described above separates the space 3 for containing the liquid specimen in the measuring cell 2 and the chamber 50 for containing the fluid from each other as well as from the outside, completely defining the shape 3 and the space 50 and, further, serves to communicate or connect the chamber 3 with the passages 35, 36 in the conduit bodies 14, 20 in a liquid-tight manner.

The top ends of the end parts 7, 8 of the measurement cell 2 may be protruded radially outwardly penetrating through the holes 70, 71 of the gasket 42 liquid-tightly to be communicated with the conduit blocks 9, 10 by the other liquid-tight connecting means respectively.

Positioning members 72, 73 are disposed respectively between the end parts 7, 8 of the measuring cell 2 and opposing portions of the back plate 39 in order to situate or position the cell main body 4 substantially in parallel with the back plate 39. Fixing or holding means 74 is provided for clamping to fix the enclosure members 54, 56 integrally to each other and for ensuring the sealing effect of the gasket 42, 40 to each of the components. The fixing means 74 comprises four bolts 75 each secured at one end to the back cover 39, a retainer frame member 76 and four nuts 77 clamping the retainer frame member 76 to the front cover 43 in cooperation with the bolts 75. Pipes 78, 79 are provided at the side wall of the frame member 41 for recycling cooling water through the space 50 as the temperature controlling fluid.

Upon assembling the electrophoretic measurement cell unit 1 having the above-mentioned constructions, the back cover 39 is placed, for instance, on an adequate base and, after disposing the gasket 40 at a predetermined position on the back cover 39, the frame member 41 and the positioning members 72, 73 are disposed at respective predetermined positions on the gasket 40 or in the openings within the annular gasket 40.

While on the other hand, the end parts 7, 8 of the measurement cell 2 are fitted from the inside into the penetrating holes 70, 71 in the U-shaped gasket parts 62, 63 of the gasket 42 by adequately distorting the gasket 42, and the tubes 16, 22 are fitted from the outside into the penetrating holes 70, 71.

The gasket 42 thus fitted with the cell 2 and the tubes 16, 22 is engaged or fitted into the grooves 58, 60 and 61 in the frame member 41, and the tubular end parts 7, 8 of the measurement cell 2 are disposed into the semi-cylindrical grooves at ends of the positioning members 72, 73 while adjusting the positions of the members 72, 73. Then, the front cover 43 is placed on the frame member 41 engaged with the gasket 42 and, further, the frame member 76 is placed on the front cover 43 and secured thereto by the threading engagement of the nuts 77 with the bolts 75 in the direction perpendicular to the longitudinal direction of the measurement cell 2. The sealing effects by the seal members 40, 42 are ensured by this threading engagement.

While on the other hand, the electrophoretic measurement cell unit 1 can be disassembled by placing the back plate 39 of cell unit 1, for instance, on a horizontal base, releasing the threaded engagement between the bolts 75 and nuts 77, removing the retainer frame member 76 and the front cover 43, then taking out the gasket 42 out of the frame member 41 and detaching the tubes 16, 22 from the gasket 42 and detaching the measurement cell 2 from the gasket 42.

As described above, in the measurement cell unit 1, since each of the components or members are merely stacked and clamped between the back cover 39 and the retainer frame member 76 in the direction perpendicular to the longitudinal direction of the measurement cell 2 fitted in the holes 70, 71 of the gasket 42, the measurement cell 2 can be assembled and disassembled or detached easily and surely with less fear of damaging the cell 2.

Upon assembling and detaching or disassembling the measurement cell unit 1, the order of mounting or detaching the measurement cell 2 and the tubes 16, 22 to and from the gasket 42, mounting and detaching of the gasket 42 to and from the frame member 41 and the like can be optionally changed.

The electrophoretic measurement cell unit 1 having thus been constituted is mounted, for instance, in such a manner that the edge 39a of the back cover 39 is situated horizontally on the upper side and that the edge 39b thereof is situated horizontally on the lower side.

After mounting the cell unit 1, the valves 12 and 18 are opened and, after charging or introducing the liquid specimen into all the regions or spaces including the cell 2 between the valves 12 and 18, the valves 12 and 18 are closed. While on the other hand, the electrolytic solution is circulated through the electrode chambers 27, 28 and cooling water is circulated through the chamber 50.

Then, an appropriate voltage is applied across the electrodes 25, 26. Alternatively, a constant electric current may be flowed between the electrodes 25 and 26 detecting the voltage gradient in the measurement cell 2 by a pair of probes. Then, the electrophoretic properties, such as velocities and electrophoretic mobility, of particles in the liquid specimen in the cell main body 4 is observed by way of the window 49 by means of a microscope (not shown) which may be connected to the video means for the electronic data processing of the observed electrophoretic information.

The region of the liquid specimen within the view of the microscope can be changed by displacing the unit 1 entirely with respect to the microscope by way of the support member 39c in the direction A or B.

Figure 5:
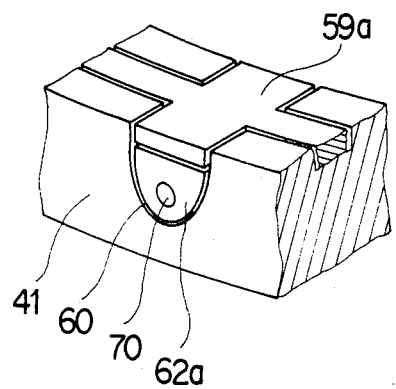
FIG. 5 is a perspective explanatory view showing a part of a modified embodiment of the gasket shown in FIG. 4.

Although the gasket parts 59, 62, 63 of the gasket 42 are formed integrally in the previous embodiment which is specifically shown in FIG. 4, they may be formed as separate gasket members such as 59a, 62a in a modified embodiment as shown in FIG. 5.

Furthermore, the gasket 42, instead of the annular shape in the illustrated embodiment, may take any other configurations such as square or elliptic shape so long as the gasket substantially forms the closed or endless loop configuration as a whole. In this case the enclosure means 54, 55 may be formed in the similar shapes.

As described above, since the measurement cell unit according to this invention comprises sealing means in the form of an endless loop as a whole and formed with penetrating holes passing through the loop between the inside and outside of the loop at opposing positions of a circumferential wall thereof, a measuring cell adapted to be fitted at both tubular end parts thereof to the penetrating holes in the sealing means, and a pair of enclosing means in close contact at endless loop edges thereof with the opposing end faces, in the form of the endless loop, of the sealing means respectively, a space or chamber for containing or accomodating a liquid specimen and a space for containing or accomodating a temperature control fluid can be defined and separated liquid-tightly by merely fitting the both end parts of the measuring cell to the penetrating holes of the sealing means and, thereafter, holding between the pair of enclosure means the sealing means under pressure or force in the direction perpendicular to the end faces of the sealing means, whereby the measurement cell can be mounted easily and securely at a desired position.

What is claimed is:

1. A cell unit for observing electrophoresis, said cell unit comprising:
 (a) an electrophoretic measurement cell;
 (b) first fluid conduit means for introducing a fluid specimen into said electrophoretic measurement cell;
 (c) second fluid conduit means for removing a fluid specimen from said electrophoretic measurement cell;
 (d) first and second enclosure means for enclosing said electrophoretic measurement cell;
 (e) a gasket seal means in the form of an endless loop disposed between said first and second enclosure means and providing a fluid-tight seal therebetween, said gasket seal means having penetrating holes therethrough through which said first and second fluid conduit means pass in a fluid-tight fashion, and;
 (f) said first and second enclosure means and said gasket seal means together defining a space in thermal contact with said electrophoretic measurement cell for accomodating a fluid used to control the temperature of a liquid specimen in said electrophoretic measurement cell.

2. A cell unit as recited in claim 1 wherein said gasket seal means is circular in shape and said penetrating holes are diametrically opposite each other.

3. A cell unit as recited in claim 1 wherein said space surrounds said electrophoretic measurement cell.

4. A cell unit as recited in claim 1 wherein one of said first and second enclosure means provides visual or electronic measurement access to said electrophoretic measurement cell.

5. A cell unit as recited in claim 1 wherein at least one of said first and second enclosure means has a groove in the surface thereof which receives at least a part of said gasket seal means therein.

6. A cell unit as recited in claim 1 wherein said gasket seal means is unitary in construction.

7. A cell unit as recited in claim 1 wherein the portions of said gasket seal means through which said penetrating holes pass are enlarged relative to the remainder of said gasket seal means.

8. A cell unit as recited in claim 7 wherein said portion of said gasket seal means have U-shaped profiles in the planes perpendicular to said penetrating holes.

9. A cell unit as recited in claim 7 wherein said portions are separate pieces distinct from the remainder of said gasket seal means.

10. A cell unit as recited in claim 1 and further comprising a pair of positioning members which support said electrophoretic measurement cell, each of said positioning members being disposed in said space between one of said fluid conduit means and one of said enclosure means.

11. A cell unit as recited in claim 1 wherein one of said enclosure means comprises a flat plate and the other of said enclosure means comprises a tubular frame element the end of which remote from said electrophoretic measurement cell is closed.

12. A cell unit as recited in claim 1 wherein one of said enclosure means comprises a flat plate and the other of said enclosure means comprises a tubular frame element and a separate plate member for closing the end of said tubular frame element remote from said electrophoretic measurement cell.

13. A cell unit as recited in claim 1 and further comprising a fixing means for fixing said electrophoretic measurement cell between said first and second enclosure means by a force in a direction which compresses said gasket seal means between said first and second enclosure means.

14. A cell unit as recited in claim 1 and further comprising a third fluid conduit means for introducing a fluid into said space and a fourth fluid conduit means for removing the fluid from said space.

15. A cell unit as recited in claim 1 wherein said gasket seal means is generally planar and is at least generally circular in shape.

16. A cell unit as recited in claim 1 wherein at least one of said first and second enclosure means has a window for microscopic observation of a specimen in said electrophoretic measurement cell.

* * * * *